United States Patent
Osypka et al.

(10) Patent No.: US 9,433,794 B2
(45) Date of Patent: Sep. 6, 2016

(54) PULSE GENERATOR SYSTEM AND METHOD FOR MEDICAL USE

(71) Applicant: Osypka Medical GmbH, Berlin (DE)

(72) Inventors: Markus J. Osypka, La Jolla, CA (US); Clemens Feige, Berlin (DE); Marcel D. Gestewitz, Berlin (DE); Thomas Fiedler, Berlin (DE)

(73) Assignee: OSYPKA MEDICAL GMBH, Berlin (DE)

( * ) Notice: Subject to any disclaimer, the term of this patent is extended or adjusted under 35 U.S.C. 154(b) by 0 days.

(21) Appl. No.: 14/666,006

(22) Filed: Mar. 23, 2015

(65) Prior Publication Data

US 2015/0273220 A1    Oct. 1, 2015

Related U.S. Application Data

(60) Provisional application No. 61/973,080, filed on Mar. 31, 2014.

(51) Int. Cl.
*A61N 1/00* (2006.01)
*A61N 1/37* (2006.01)
*A61N 1/372* (2006.01)
*A61N 1/362* (2006.01)
*A61N 1/39* (2006.01)

(52) U.S. Cl.
CPC .......... *A61N 1/3712* (2013.01); *A61N 1/3625* (2013.01); *A61N 1/37247* (2013.01); *A61N 1/3993* (2013.01)

(58) Field of Classification Search
CPC .............. A61N 1/37205; A61N 1/37247; A61N 1/3625; A61N 1/3712; A61N 1/3686; A61N 1/36142; A61N 1/36146; A61N 1/37235; A61N 1/36071; A61N 1/36185
See application file for complete search history.

(56) References Cited

U.S. PATENT DOCUMENTS

| | | | |
|---|---|---|---|
| 2004/0064161 A1* | 4/2004 | Gunderson | A61B 5/0424 607/28 |
| 2011/0208265 A1* | 8/2011 | Erickson | A61N 1/37247 607/46 |
| 2012/0101546 A1* | 4/2012 | Stadler | A61N 1/3712 607/28 |
| 2012/0109254 A1* | 5/2012 | King | A61N 1/36185 607/46 |
| 2014/0303689 A1* | 10/2014 | Steinke | A61N 1/36142 607/59 |

OTHER PUBLICATIONS

Sulzbach LM, Landsdowne LM; Temporary atrial pacing after cardiac surgery, Focus Crit Care, Feb. 18, 1992(1): 65, 68-74.

(Continued)

*Primary Examiner* — Robert N Wieland
(74) *Attorney, Agent, or Firm* — Procopio, Cory, Hargreaves & Savitch, LLP

(57) ABSTRACT

An electrical pulse generator system such as a cardiac pacemaker or defibrillator system includes an impedance measuring device which measures the impedance across pacemaker leads, a display device, and a controller which controls the display device to display at least the measured impedance upon each stimulation pulse, or an image showing the relationship between a first applied electrical signal, measured impedance, and a resulting electrical signal which varies according to Ohm's Law. The system may include a short circuit detector and a pulse amplitude control module which switches between normal mode and safe mode operation based on short circuit detection, with different maximum stimulation pulse amplitudes in the normal and safe modes.

14 Claims, 12 Drawing Sheets

(56) References Cited

OTHER PUBLICATIONS

M.C. Reade, Temporary epicardial pacing after cardiac surgery: a practical review, Part 1: General considerations in the management of epicardial pacing; Anaesthesia, 2007, 62, pp. 264-271; GB and Ireland.

M.C. Reade, Temporary epicardial pacing after cardiac surgery: a practical review, Part 2: Selection of epicardial pacing modes and troubleshooting; Anaesthesia, 2007, 62, pp. 364-373; GB and Ireland.

Gupta et al; Predictors for use of temporary epicardial pacing wires after pediatric cardiac surgery; The Journal of Thoracic and Cardiovascular Surgery, vol. 144, No. 3.

Sulzbach LM, Landsdowne LM; Temporary atrial pacing after cardiac surgery, Abstract, Focus Crit Care, Feb. 18, 1992(1): 65, 68-74.

Principles of Pacemaker-Myocardial Interaction; Moses-Mullin, Chapter 3, pp. 43-57.

Boston Scientific Corporation; Ensuring Successful Lead Impedance Measurements in Boston Scientific Pacemakers; Mar. 24, 2009.

Hurle, A. et al.; Optical Location for Temporary Epicardial Pacing Leads Following Open Hear Surgery, Journal of Pacing and Clinical Electrophysiology, vol. 25, No. 7, Jul. 2002, pp. 1049-1052.

Mahon, Linda et al.; Cardiac Tamponade After Removal of Temporary Pacer Wires; American Journal of Critical Care, Nov. 2012, vol. 21, No. 6, pp. 432-441.

Del Niod, Pedro et al.; Temporary Epicardial Pacing after Open Heart Surgery: Compilations and Preventions; Journal of Cardiac Surgery 4:99-103, Mar. 1989, pp. 99-103.

Sakellaridis, Timothy et al.; Bilateral sternobronchial fistula after coronary surgery—are the retained epicardial pacing wires response? a case report; Journal of Cardiothoracic Surgery, Jun. 24, 2009.

\* cited by examiner

PULSE GENERATOR SYSTEM AND METHOD FOR MEDICAL USE

BACKGROUND

1. Field of the Invention

This invention relates generally to pulse generators and is particularly concerned with pulse generator or pacemaker/defibrillator systems and methods for cardiac applications (cardiac rhythm management), as well as display devices and methods for set up and monitoring operation of external pacemakers/defibrillators.

2. Related Art

Pulse generators in general but in particular for cardiac applications usually generate an output of specific rate, amplitude and duration of the pulse. Amplitude refers either to a voltage (for instance 0 . . . 18 V) or a current (for instance, 0 . . . 25 mA) and is specified for a load or impedance range (for instance, 200 . . . 2,000Ω).

Pulse generators for cardiac applications are referred to as pacemakers. The impedance, or load, a pacemaker is facing is determined by the impedance of the lead wires and possible extensions thereof, the impedance of the heart tissue (myocardium, epicardium), and the impedances of the electrode-tissue interfaces (for a pair of electrodes). The impedance of the lead wires is usually of resistive nature and is generally a few ohms (for instance, approximately 10 ohms for a unipolar myocardial pacing wire with a length of 60 cm). The impedance of the heart tissue depends on the distance between the electrodes and also measures several tens or hundreds of ohms.

The impedance of the electrode-tissue interfaces is determined by their effective surface area. The impedance of an electrode-tissue interface of a unipolar myocardial pacing wire with an electrode length of 10 mm, for instance, may measure 100 ohms or more. Variations in strength of the electrode-tissue contact and manipulation of the pacing wire insulation may lead to an increase or decrease of the electrode-tissue impedance.

If the impedance of a stimulation system is outside the specified range, the pacemaker may not be able to maintain the desired stimulation voltage or current. It is thus of importance to the operator of a pacemaker to know the impedance the pacemaker is facing.

Temporary cardiac stimulation is the preferred method of treating temporary rhythm disturbances which can potentially follow cardiac surgery. In view of this risk, prior to chest closure after cardiac surgery, a pair of unipolar pacing wires or a single bipolar pacing wire is attached to, or sutured onto, the outside of the heart chamber (epicardium or myocardium) to allow for cardiac stimulation, for example to the right atrium and right and left ventricle. The other end of the pacing wires is fed through the chest outside the patient's body for connection to a temporary pacemaker (also referred to as external pulse generator, or EPG) directly or via extension cables. Post cardiac surgery when temporary cardiac stimulation is not needed any more, pacing wires are removed simply by pulling the wires out of the patient's chest.

Pacing wires, also known as heart wires, come in various configurations. A very important property is the means of fixing or attaching the wire onto the heart. The fixation needs to be designed in such a way that a wire stays securely at the intended location but can be removed easily post cardiac surgery. Non-traumatic wires simply attach to the heart with or without suturing. Pacing wires with a zig-zag fixation rely on bending a portion of the distal wire into a zig-zag shape. Other pacing wires are designed so that a portion of the distal plastic insulation is peeled off in order to form tines or wings which secure the position of the wire onto the heart muscle. The bare wire, i.e., the portion of the wire without insulation, acts as the active electrode for stimulation.

Obviously, there is a fine line between secure fixation and easy removal of the wire. In a few instances removal of pacing wires incorporating tines (or wings) for fixation reportedly caused bleeding and cardiac tamponade. After the pacing wire is attached to the heart muscle, the wire's cardiac needle and some portion of the wire is cut off. It is up to the discretion of the cardiac surgeon how much of the wire is cut off and whether the distal portion of the insulation including the tines (or wings) remains in place or not. Obviously, liberal manipulation of the distal end of the pacing wire can result in a significant increase of the length and surface area of the bare wire, thus changing the electrical properties of the stimulation system, which in turn may affect the performance of the external pacemaker and jeopardize stimulation therapy.

SUMMARY

In one aspect, an electrical pulse generator such as a cardiac pacemaker and/or defibrillator includes a display device and a controller which controls the display device to display an image showing the relationship between a first applied electrical signal, measured impedance, and a resulting electrical signal which varies depending on the first electrical signal and the measured impedance, according to Ohm's Law.

In one embodiment, the first electrical signal is a voltage which can be varied by the operator of the pulse generator, and the second electrical signal is the current which varies as a function of the first electrical signal and the measured impedance. In another embodiment, the first electrical signal is a current which can be varied by the operator of the pulse generator, and the second electrical signal is a voltage which varies as a function of the current and measured impedance.

If the electrical pulse generator incorporates a constant/adjustable voltage source, one embodiment of the display device displays an image of the relationship:

$$(\text{Voltage (V)})/(\text{Impedance }(\Omega))=(\text{Current (A)}).$$

If the electrical pulse generator incorporates a constant/adjustable current source, another embodiment displays an image of the relationship:

$$(\text{Current (A)})*(\text{Impedance }(\Omega))=\text{Voltage (V)}.$$

In another aspect, a system and method is provided for set up and monitoring of the electrical pulse generator. The pulse generator or pacemaker has a first electrical signal of amplitude adjustable by an operator and a stimulation lead system is provided for connection of the pulse generator output to a patient undergoing stimulation therapy. The system further comprises a display device which displays the current amplitude of the first electrical signal (which may be voltage or current), the detected impedance when the stimulation lead system is placed for application of stimulation therapy to a patient, and the resultant second electrical signal (current or voltage). This system may be used in initial placement of stimulation leads at the heart, for example following cardiac surgery, so that the operator or surgeon can position the stimulation leads appropriately in order to ensure that the detected impedance is within the recommended range for the pulse generator or cardiac pacemaker. It can also be used to monitor the level of the second electrical signal during operation of the pulse generator, for example when the operator adjusts the first electrical signal.

The method and apparatus in one embodiment comprises an external pulse generator, or pacemaker, which determines impedance of the lead stimulation system upon each stimulation pulse, adjusts the stimulation amplitude according to impedance if needed, and communicates the applied voltage and current and as well as the impedance to the operator.

Other features and advantages of the present invention will become more readily apparent to those of ordinary skill in the art after reviewing the following detailed description and accompanying drawings.

BRIEF DESCRIPTION OF THE DRAWINGS

The details of the present invention, both as to its structure and operation, may be gleaned in part by study of the accompanying drawings, in which like reference numerals refer to like parts, and in which.

DETAILED DESCRIPTION

Certain embodiments as disclosed herein provide for an electrical pulse generator system for medical use, such as a cardiac pacemaker or a defibrillator, the system having a first electrical signal of amplitude adjustable by an operator, a stimulation lead system for connection to a patient undergoing stimulation therapy, an impedance measuring device connected to the stimulation lead system, and a display device which displays the current measured impedance at each stimulation pulse.

After reading this description it will become apparent to one skilled in the art how to implement the invention in various alternative embodiments and alternative applications. However, although various embodiments of the present invention will be described herein, it is understood that these embodiments are presented by way of example only, and not limitation.

Figure 1:
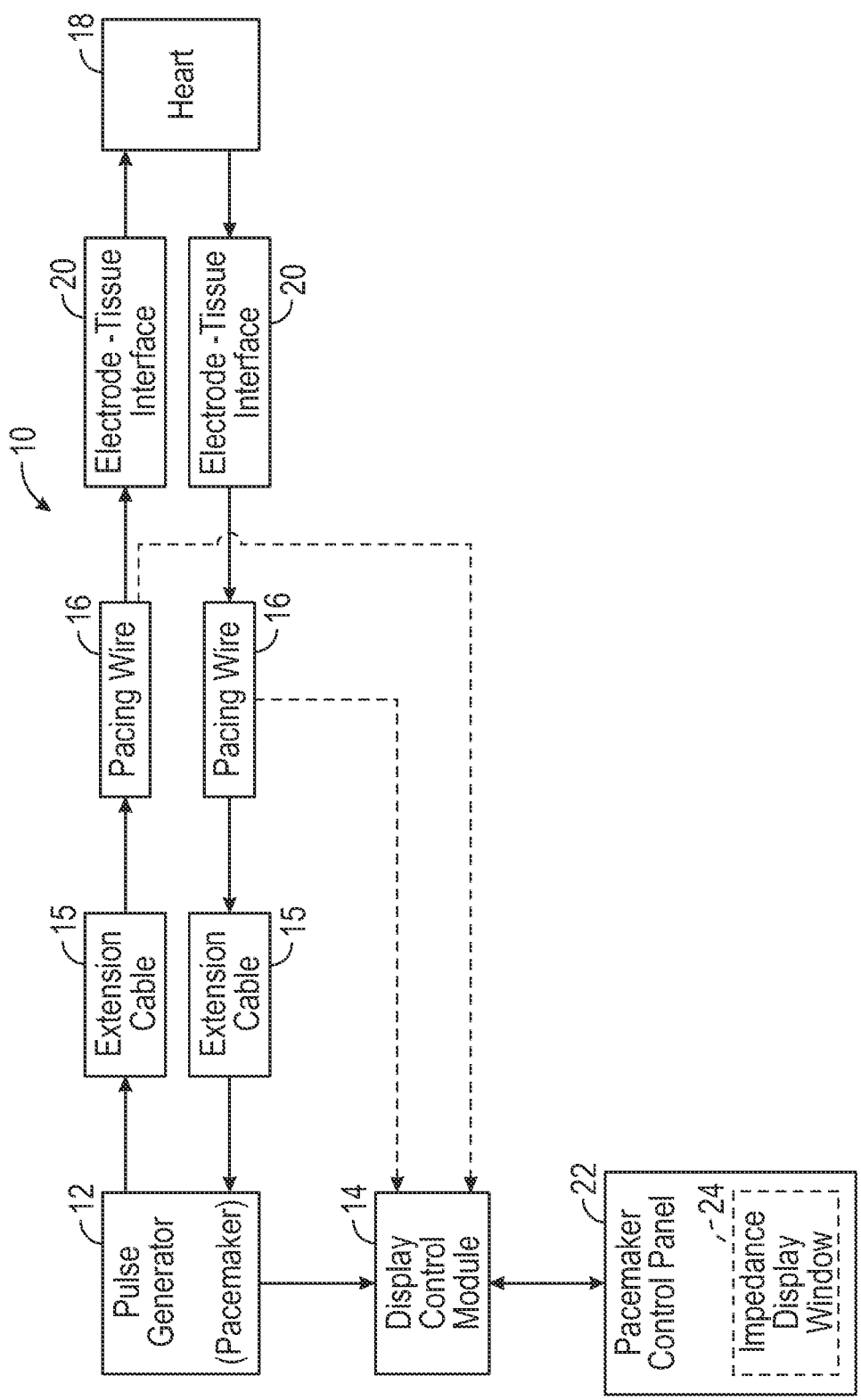
FIG. 1 is a block diagram of one embodiment of a cardiac stimulation or pacemaker system incorporating a display device.
Figure 2:
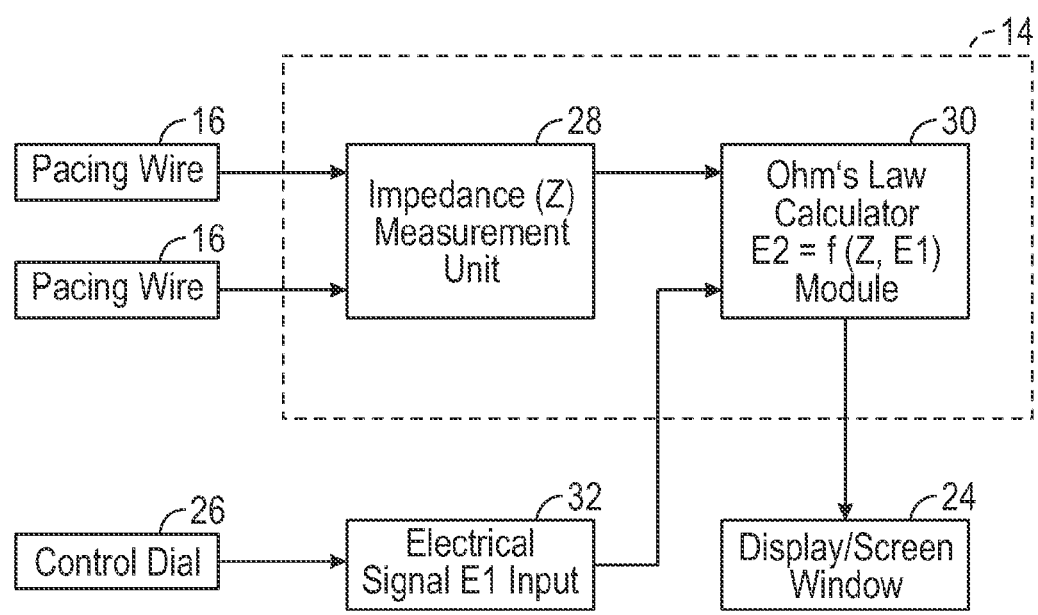
FIG. 2 is a block diagram of one embodiment of an impedance monitoring and Ohm's law display system incorporated in the cardiac pacemaker system of FIG. 1.
Figure 3:
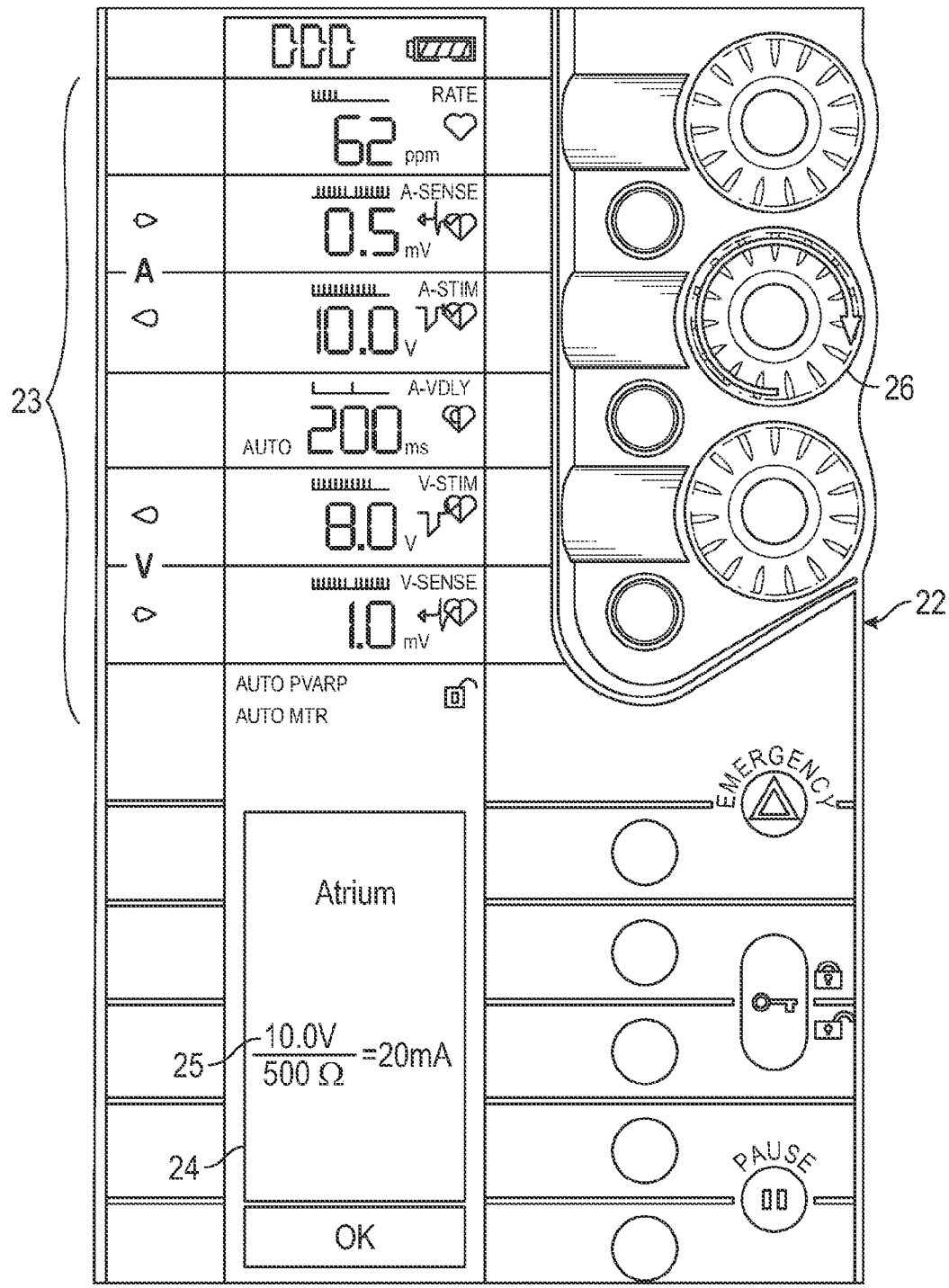
FIG. 3 is a front elevation view of a control panel associated with the pulse generator or pacemaker of FIG. 1 including a display controlled by the system of FIG. 2 to indicate electrical signal levels and impedance of the pacemaker system according to Ohm's law.

FIG. 1 illustrates one embodiment of a pacemaker or pulse generator system 10 comprising pulse generator or cardiac pacemaker 12, extension cables 15, pacing wires 16 connected to the extension cables at one end and to the heart 18 of a patient at electrode tissue interfaces 20, and a display controller or control module 14 which controls an output display device 24 to display current measured impedance at each stimulation pulse as part of an Ohm's law relationship, as described in more detail below. FIG. 2 illustrates one embodiment of the display control module 14 of FIG. 1. FIG. 3 illustrates one embodiment of a control panel 22 for the pacemaker's control/display module which includes display screen or window 24 which displays the current Ohm's law relationship 25 between a first electrical signal or parameter E1 (in this case voltage), detected impedance Ω (Ohms), and the resultant second electrical signal E2 (in this case current), as determined by the impedance monitoring and display control module of FIG. 2. Note that the current is displayed in mA in this embodiment, by multiplying the resultant current in amps by $10^3$. However, the current may be displayed directly in amps in other embodiments. In an alternative embodiment, instead of displaying the relationship of voltage, impedance and current, an approximate value of the measured impedance can be indicated by an array of LEDs.

Also provided on display panel are various pulse parameters such as pulse rate, stimulating signal E1 (in this case voltage), control buttons, and a control dial 26 for operator adjustment of the stimulating input signal or voltage. The arrangement of the parameters voltage, impedance and current in the Ohm's law relationship 25 illustrated in FIG. 3 is one embodiment for a pacemaker providing the voltage as a first electrical signal or parameter E1 because it displays the unknown current in form of a result. It will be understood that any other arrangement of these parameters which fulfills Ohm's law is applicable in alternative embodiments. Also, the measured impedance value alone may be displayed in other embodiments.

As illustrated in FIG. 2, the impedance monitoring/display control module or processing unit 14 has an impedance detection/measurement unit 28 connected to the pacing wires 16 or pacemaker lead system for measuring the impedance Z, which is a combination of the impedance of the lead wires themselves, the impedance of the heart tissue between the wires or electrodes, and the impedances at the electrodes 20 (electrode-tissue interfaces). The geometrical length or surface area of the electrodes determines the current density within the tissue and thus the impedances at the electrode-tissue interface. The amount of heart tissue impedance is dependent on the distance between the electrodes and the length of the electrodes. In this embodiment, the processing unit or system 14 also includes an Ohm's law calculator module 30 which has a first input connected to the output of the impedance measurement unit 28 and a second input 32 corresponding to the stimulation signal amplitude. The Ohm's law calculator 30 in FIG. 2 can be arranged in any of the following ways:

E1/Z=E2 or E1*Z=E2, depending on the nature, voltage or current, of E1 and E2.

One may also write E2 as math function from E1 and Z: E2=f(E1, Z).

In this embodiment, E1 varies in response to operator adjustment of control dial 26 on the control panel to set the pacing amplitude (voltage amount) but may be limited automatically in some circumstances, as described in more detail below in connection with the embodiment of FIGS. 5 to 8.

With the system of FIGS. 1 to 3, when the operator turns the dial or knob 26 for setting the atrial output signal, the message window or display screen 24 in the lower portion of the display shows all current values for the atrial output signal, detected impedance, and current. In an alternative embodiment, the measured impedance only is displayed as each adjustment in pacing amplitude is made. A similar design is implemented for other stimulation channels of the pacemaker. In one embodiment, the components of the pulse generator/pacemaker and display generating system may be incorporated in a single unit or housing with the display and control panel of FIG. 3 mounted on a suitable surface of the unit or housing. This tool allows the impedance of the pacing system to be determined in the operating room during heart surgery, while the surgeon still has the opportunity to rearrange the pacing wires for impedance adjustment.

Figure 4:
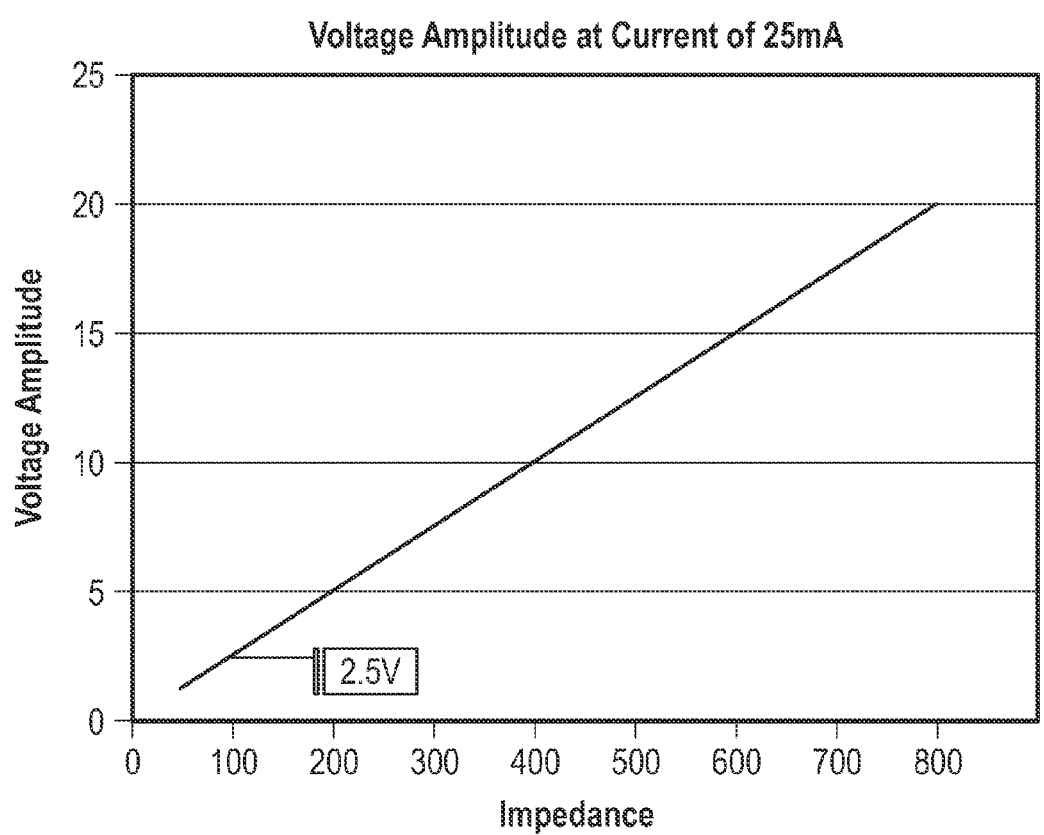
FIG. 4 is a graph of voltage versus impedance of the system of FIGS. 1 to 3, at a constant current amplitude of 25 mA.

Commonly the specified operation range for the impedance of the stimulation lead system (i.e. pacing wires, tissue-electrode interfaces, heart tissue, and extension cables) for external pacemakers is 200 . . . 2,000Ω. Note that a sufficient voltage level, not the current level, primarily causes depolarization of the heart cells, a phenomenon also referred to as capture. FIG. 4 is a graph illustrating the voltage (y-axis) over impedance (x-axis) assuming a constant current amplitude of 25 mA (maximum current output of commonly used external pacemakers). At an impedance of 100Ω, the resulting stimulation voltage is only 2.5 V, which may or may not be sufficient to obtain capture. If the impedance of a stimulation lead system is lower than the specified lower range limit, the pacemaker may not be able to maintain the desired stimulation voltage or current. Clearly, a low impedance stimulation lead system may lead to complications in stimulation therapy and adverse events in patients who are pacemaker-dependent. It is thus of importance to the operator of a pacemaker to know the current impedance value of the stimulation system. Currently available prior art external pacemakers only allow the user to set the stimulation amplitude, which is either a voltage or current. Due to the lack of an impedance measurement, the operator has no feedback about the arrangement and electrical properties of the pacing wires.

Thus, the system and method described above in connection with FIGS. 1 to 3 provides a tool for evaluation of proper arrangement of pacing wires encompassing their intrinsic electrical properties as well as the proximity of the stimulation electrodes. Additionally, in the system of FIGS. 1 to 3, the external pulse generator or pacemaker includes an impedance monitor to determine the impedance of the lead stimulation system on each stimulation pulse, and a processor which calculates and displays the actual applied stimulation amplitude (which is voltage in the illustrated embodiment), the measured impedance, and the resulting electrical signal derived from Ohm's law (i.e. current in the illustrated embodiment) to the operator.

Table 1 below illustrates one example of test results using the above system to take impedance measurements using different pairs of unipolar temporary pacing wires in conjunction with post cardiac surgery external pacemakers, where the distance between the electrodes of a pair and the electrode length (and thus surface area) was varied. Shorter distance between the electrodes or pacing wires and larger electrode surface area correlated with a lower impedance measurement.

TABLE 1

| Distance between pacing wires | Measured Impedance Ω Setup 1 (pacing wire type 1, length 10 mm) | Measured Impedance Ω Setup 1 (pacing wire type 2, length 10 mm) | Measured Impedance Ω Setup 2 (pacing wire type 2, one 10 mm, one 50 mm) | Measured Impedance Ω Setup 3 (pacing wire type 2, both 50 mm) |
|---|---|---|---|---|
| 50 mm | 646-649 | 590-596 | 192 | — |
| 40 mm | 623 | 505-508 | 198 | — |
| 30 mm | 561-571 | 320-328 | 219 | — |
| 20 mm | 397 | 311-324 | 203 | — |
| 10 mm | 310 | 245 | 236 | 68 |
| 5 mm | — | — | 233 | — |

The pacing wires used in obtaining the test results of Table 1 were as follows:

Type 1: TME 60 TC manufactured by Oscor of Palm Harbor, Fla.

Type 2: MYO/WIRE™ M-25 style, Manufactured by A&E Medical of Farmington, N.J.

The type 2 wire was used for set up 2 and 3, with the exposed length of one wire being 10 mm and the other wire 50 mm in set up 2, and both wires having an exposed length of 50 mm in set up 3. The wires were placed into a beef sample to simulate heart tissue in order to measure variation in impedance.

As shown by the results of the aforementioned experiment and seen in clinical practice, stimulation lead systems do occasionally exhibit impedances significantly lower than the specified minimum for the pacemaker's preferred impedance range (typically 100 or 200 ohms), which may compromise the intended stimulation therapy. As seen in Table 1, greater exposed lengths of stimulation leads as well as reduced spacing between the leads results in lower impedance, potential short circuit conditions and possible clinical pacing failure. Based on Ohm's law, the lower the impedance, the more current is drawn from the pacemaker at a given voltage, and the less voltage that is available for successful capture at a given current. The impedance monitoring tool described above in connection with FIGS. 1 to 3 allows the impedance of a temporary post-surgery pacing system to be determined in the operating room, while the surgeon still has the opportunity to change the pacing wire placement to produce higher impedance values and thus reduce the risk of pacing failures.

In the embodiments of FIGS. 5 to 10, the determined impedance in the first embodiment is used as an additional control for the stimulation amplitude, thus maximizing the ability of the pacemaker to meet the intended stimulation therapy. This is accomplished by controlling the maximum applicable stimulation amplitude, taking into consideration the nominal amplitude set by the operator and pacemaker circuit conditions.

Figure 5:
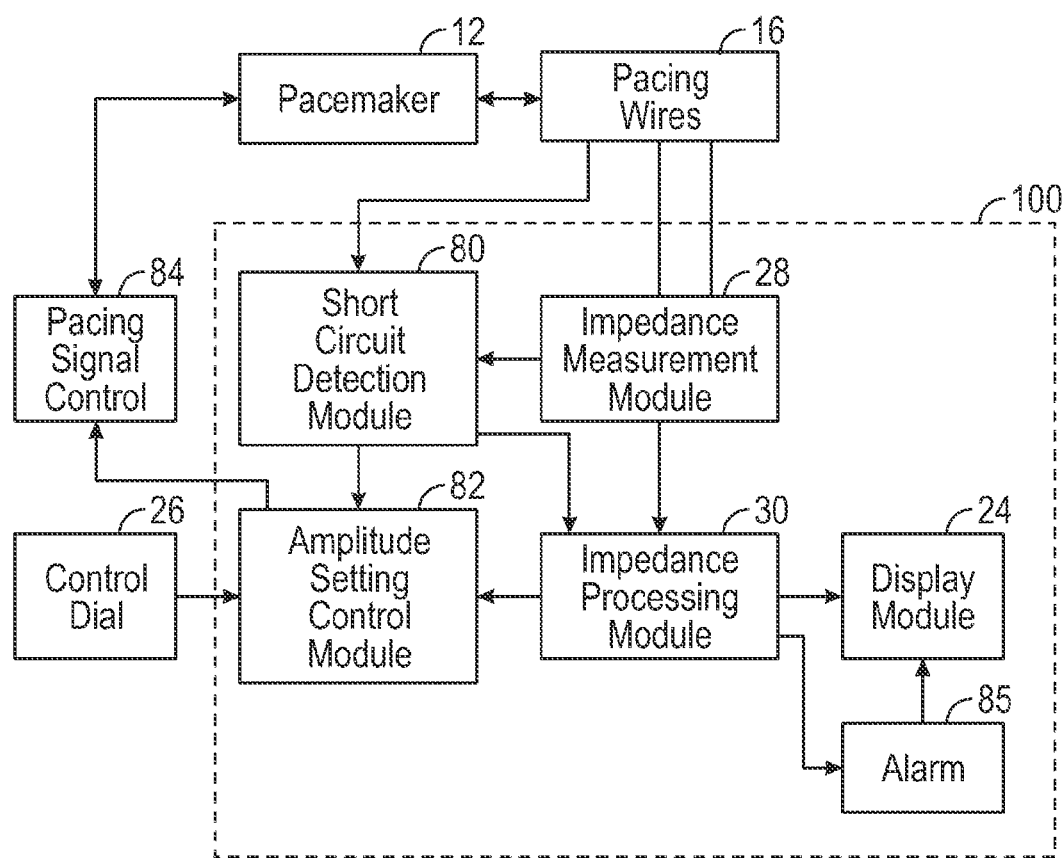
FIG. 5 illustrates one embodiment of a pacemaker amplitude control system including normal mode and safe mode operation.
Figure 6:
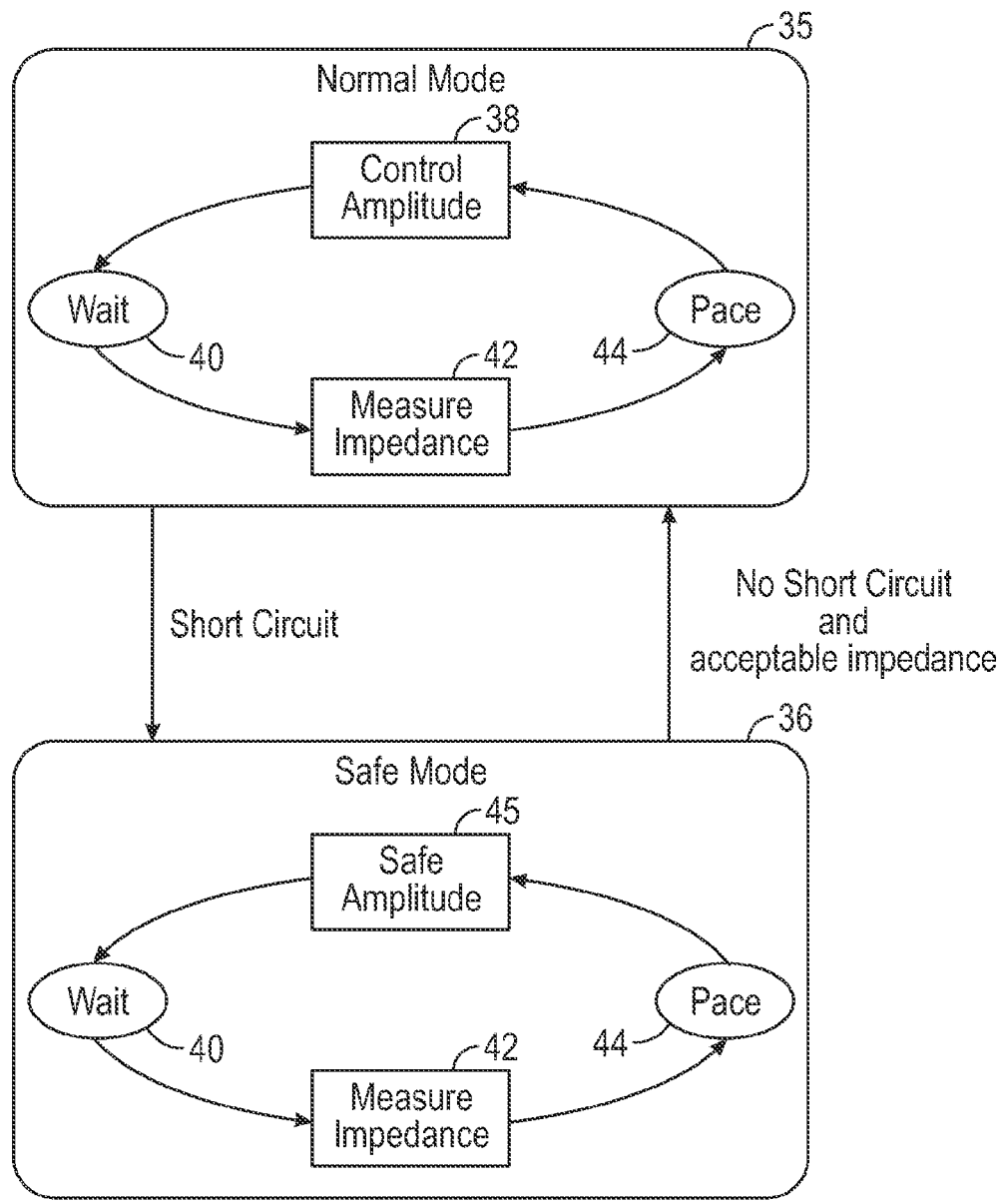
FIG. 6 is a flow diagram illustrating normal and safe mode operation of the pacemaker using the control system of FIG. 5.
Figure 7A:
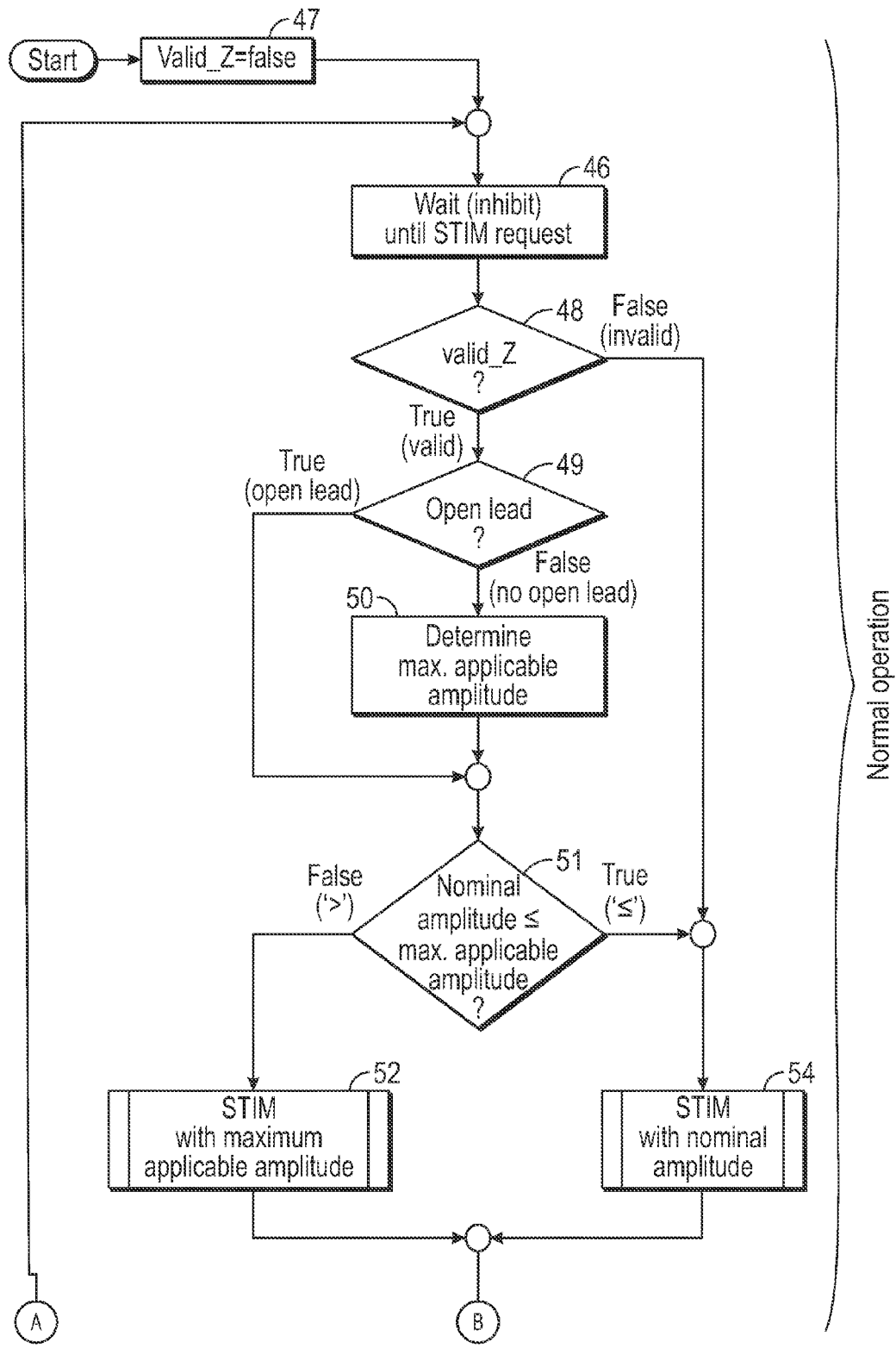
FIGS. 7A and 7B are successive parts of a more detailed flow diagram illustrating normal and safe mode operation of a cardiac stimulation system using the control system of FIG. 5.
Figure 7B:
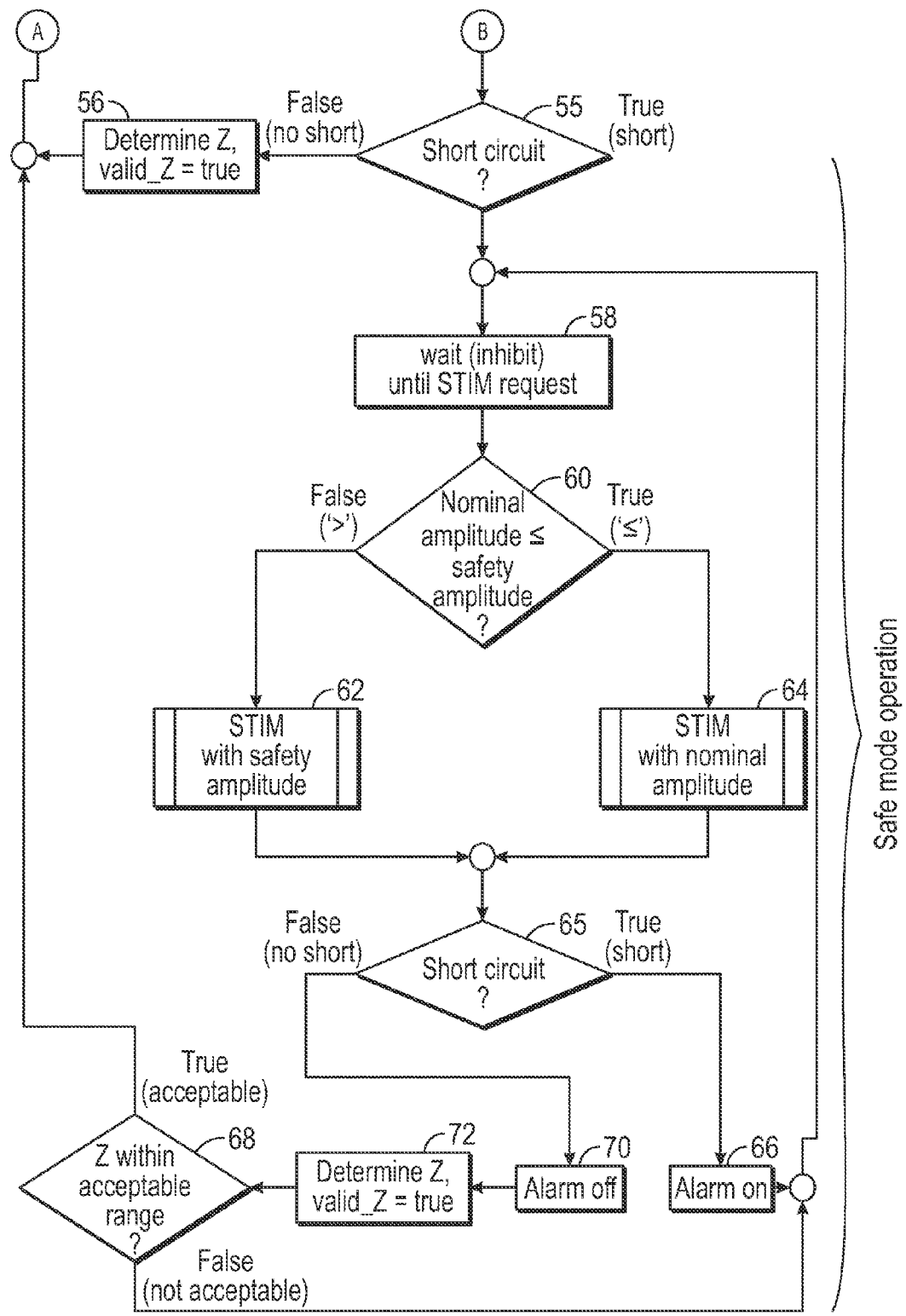

FIG. 5 illustrates one embodiment of a monitoring and cardiac stimulation control system 100 for a pacemaker, which defines a 'normal mode' and a 'safe mode' for stimulation therapy, while FIG. 6 is a flow diagram illustrating the normal mode 35 and safe mode 36. FIGS. 7A and 7B illustrate successive parts of a more detailed flow diagram illustrating operation of the cardiac stimulation control system 100. In the system of FIGS. 5 to 7B, 'Normal Mode' is defined as a mode within which the electrical signal amplitude (referred to as "nominal amplitude") is set by an operator, for example using the control dial 26 of FIG. 3. The nominal amplitude is equal to or less than the maximum applicable amplitude which is limited based on measured impedance. In contrast, 'Safe Mode' is defined as a mode in which the stimulation amplitude is limited to a pre-defined level (safety amplitude) to allow the pacemaker to stimulate effectively at low impedances. Both 'Normal Mode' and 'Safe Mode' incorporate amplitude control. In 'Normal Mode' the control method is based on measured impedance, while in 'Safe Mode' the control method is not based on measured impedance. The latter control method especially considers the fact that the impedance may not be known (or recently obtained) at any given time, and in consequence the impedance based amplitude control may not always be reliable.

The switch from 'Normal Mode' to 'Safe Mode' is made by a decision or control system 100 as illustrated in FIG. 5, which may be implemented in hardware in one embodiment, but which may be implemented by other means such as software or a combination of software and hardware in other embodiments. As illustrated in FIG. 5, control system 100 comprises impedance measuring module 28 and impedance processing module/calculator 30 as in the previous embodiment, as well as a short circuit detection module 80 and an amplitude setting control module 82 which controls switching between the normal mode 35 and the safe mode 36 as well as maximum signal amplitudes in those modes, as described below in connection with FIGS. 6 to 7B. Short circuit detection module 80 determines what is referred to as a 'short circuit' condition, meaning that impedance (or applied current or voltage) has met a predefined threshold. This threshold can be met if the applied amplitude exceeds the maximum applicable amplitude (excess voltage or current) and/or the impedance is below a predefined threshold (short circuit condition). Pacemaker 12 includes a pacing signal controller 84, and the output of amplitude setting control module 82 is provided to the pacing signal controller 84 as indicated in FIG. 5.

As illustrated in FIG. 6, when no short circuit is detected by detection module 80 and the detected impedance (28, 30) is determined by the amplitude setting control module to be within acceptable minimum and maximum levels, the system operates in normal mode. In this case, the operator controls the amplitude of the stimulation signal (38) via control dial 26 or other operator input, the system waits for a stimulation request (40), after which impedance is measured (42) by module 28 during a pace or stimulation pulse (44). At any time, if a short circuit condition is detected by module 80, the system switches to safe mode 36, and the maximum applicable stimulation amplitude to be applied by pacemaker 12 is set to a pre-defined safety amplitude, so the operator can only control amplitude within the safe amplitude limit (45). In safe mode, the stimulation amplitude is limited to a pre-defined lower level (safety amplitude) to allow the pacemaker to stimulate effectively at low detected impedances. If the system returns to acceptable impedance levels and no short circuit condition, the system switches back to normal mode where amplitude is controlled by the operator.

FIGS. 7A and 7B present a detailed flow chart for the system of FIGS. 5 and 6 in which a pulse generator allows the user to control stimulation voltage (amplitude in this case is voltage). The pacemaker starts with the impedance unknown, and this condition is represented by Valid_Z=false in step 47. Note that impedance can be determined only during stimulation. The pacemaker waits for a request for stimulation 46 via pacing signal control 84. A request for stimulation, for instance, can be triggered if the nominal rate set by the user is higher than the patient's intrinsic rate, or no intrinsic rate is measured, or asynchronous stimulation is desired, but may also be triggered in other ways in alternative embodiments.

Impedance is measured during stimulation. If the impedance is within a predefined range, i.e. true or "valid" (valid_Z, step 48), and there is no open lead (49), the pacemaker determines the maximum applicable or safe amplitude (50). Sufficient voltage amplitude is required for capture with the impedance within a specified range for the particular pulse generator, for example 200-2000 Ohms (the applicable impedance range may vary from this range dependent on the pulse generator characteristics). A pulse generator providing a constant voltage (a nominal value preset by the user) may not be able to maintain a specified voltage if the impedance falls below the specified impedance range. The solution to this problem is to limit the output voltage to a preset maximum applicable amplitude. In one example, the maximum applicable amplitude may be set as 18 volts (see FIG. 8). In step 51, amplitude setting control module determines if the nominal amplitude, i.e., the amplitude set by the operator, is greater than the maximum applicable amplitude (e.g. 18 volts). If so (false), the pacemaker stimulates with the maximum applicable amplitude (52). If the nominal amplitude is equal to or less than the maximum applicable amplitude at step 51 (true), and also if the impedance at step 48 is not within a predefined range (false or invalid), the pacemaker stimulates with nominal amplitude (54). The detected impedance as well as the applied voltage or current amplitude, which can be less than the nominal amplitude, may be communicated to the operator via message displayed on display screen 24 as in FIG. 3.

A 'short circuit' detection 55 by short circuit detection module 80 (see FIGS. 5 and 7B), which may be implemented in hardware, determines an excess amplitude during stimulation. If no 'short circuit' is detected, the pacemaker has determined and controlled the amplitude accordingly, i.e. false (no short) at step 55, and the pacemaker determines the impedance Z and sets Valid_Z=true, step 56. The pacemaker returns to step 46 and waits for the next request for stimulation. Note that the 'short circuit' detection may be determined by module 80 detecting a predefined low level of impedance, or determining an excess voltage or current.

Note that 'Valid_Z' has a limited life expectancy. Even when impedance is determined to be within a predefined acceptance range, impedance may exceed this range after longer periods of inhibition. For instance, but not limited to, a life expectancy of as low as 30 seconds to several minutes may be considered. Note also the predefined acceptance range may be larger than the specified range for impedance.

If the control system determines that the detected impedance is within the predefined acceptance range but outside the specified range, a corresponding warning message may be communicated to the user.

If a 'short circuit' is detected at step 55, no impedance was obtained (Valid_Z=false). The pacemaker switches to the 'Safe Mode', i.e., a mode within which the maximum applicable amplitude is limited to a predefined level, which depends on the hardware design of the voltage source, not on impedance. This level may be in the range from 5 to 12 volts depending on the pacemaker or pulse generator, and in the example of FIG. 8 the safe mode maximum amplitude is 8 volts. The limitation of the amplitude is necessary to ensure that the pacemaker is able to provide effective stimulation for capture at impedances lower than the specified range.

One embodiment for 'Safe Mode' is illustrated in FIG. 7B, see steps 58 onwards. If the pacemaker detects a 'short circuit' situation (step 55) during the previous stimulation, it limits the applicable amplitude to a predefined level (safety amplitude). Note that the nominal or applied amplitude, i.e., the amplitude set by the operator (in this case voltage), may be less than the maximum applicable amplitude in the normal mode or less than the predefined safety amplitude in the safe mode. In either case, the operator does not see any difference between the actual amplitude shown in the message or output display window (actual voltage, current and impedance) and the nominal amplitude when below the predefined maximum level for the operation mode. This is true both in the Safe Mode and in the Normal Mode.

After switching to the Safe Mode at step 55 (True), the pacemaker waits for the next request for stimulation (58). At that point, if the nominal amplitude is above the predefined level or safety amplitude at step 60 (false), stimulation proceeds at the safety amplitude (step 62). If the nominal amplitude is below the safety amplitude at step 60 (true), stimulation proceeds at the nominal amplitude (step 64). If a 'short circuit' is detected again at step 65, the pacemaker activates an alarm 85 (see FIG. 5) and/or corresponding alarm message (step 66). After the alarm has been activated, the system returns to step 58 to wait for the next stimulation request. The alarm is reset if a 'short circuit' is not detected during the next stimulus. If no 'short circuit' is detected at step 65 any alarm is turned off (step 70), and the system determines valid_Z=true at step 72. Current impedance is evaluated to see if it is within an acceptable range (step 68). If not, the system remains in 'Safe Mode' based on the detected impedance, and returns to step 58 to wait for the next request for stimulation in the safe mode. If the impedance is determined to be within the acceptable range at step 68, the system switches to "Normal Mode" and returns to step 46 of FIG. 7A.

In this embodiment, feedback is provided to the operator at each stimulation pulse, for example via display panel or window 24 on a control panel as illustrated in FIG. 3. Each time the control for setting the stimulation amplitude of a particular channel is activated (e.g. by turning the dial knob 26 of the atrial channel), a message or display 25 appears in window 24 showing the applied voltage (in V), the impedance (in Ω) and the current (in mA). Alternatively, the display may simply show the currently determined impedance. Change in the amplitude of either voltage or current corresponds to a change in the amplitude of current or voltage, respectively, assuming impedance is constant. In the embodiment of FIG. 3, the operator sets the (nominal) voltage amplitude. Note that the actual amplitude shown in the message window may be less than the nominal amplitude set by the user (upper portion of the display) if impedance measurement or short circuit detection triggers a decrease in amplitude in the manner illustrated in FIGS. 6 to 7B.

Figure 8:
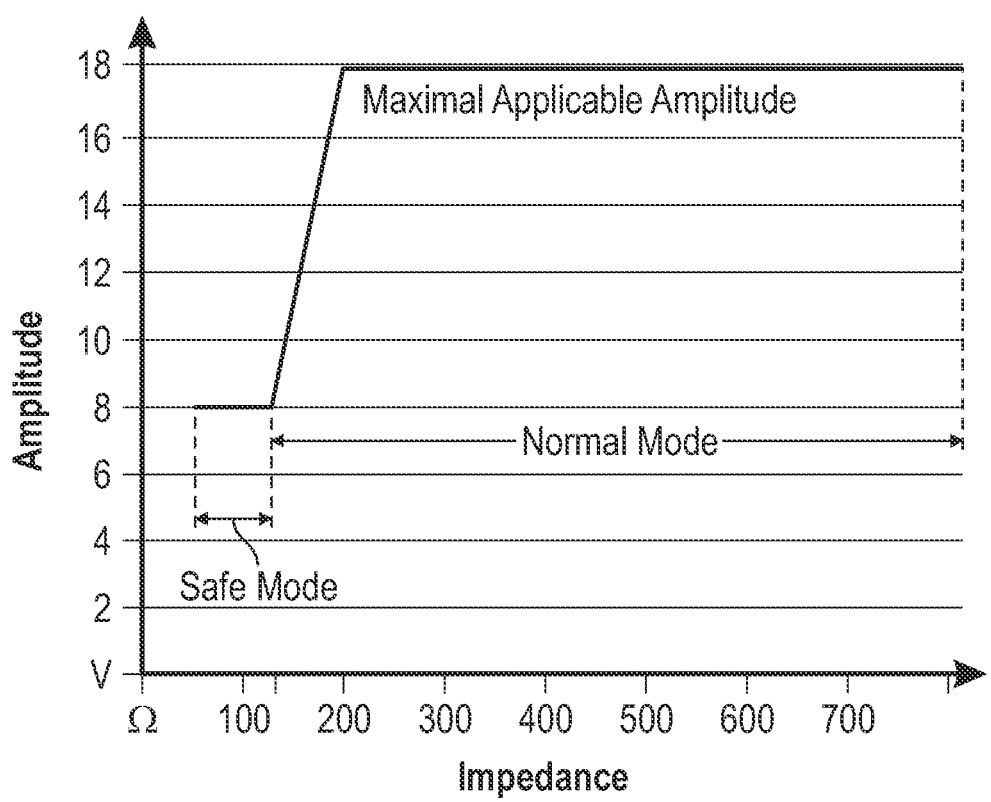
FIG. 8 is a graph illustrating variation of controllable signal amplitude with impedance in one embodiment of the system of FIG. 5 in which maximum applicable signal amplitude (e.g. voltage) is limited in normal and safe operation modes.

FIG. 8 is a graph illustrating the voltage (y-axis) over impedance (x-axis) of one embodiment within which the maximum applicable voltage amplitude (bold black line) is limited based on the determined impedance, as in FIGS. 7A and 7B. In one embodiment, a 'Normal Mode' may be defined as the impedance range from approximately 130Ω to the upper limit of the specified range (for instance, 2,000Ω), and 'Safe Mode' is applied for impedances less than 130Ω. Compared to the scenario shown in FIG. 4, the stimulation voltage in the safe mode at 100Ω is about 8 V, which offers much more 'reserve' than the 2.5 V of FIG. 4. The safety mode voltage may be set anywhere in a range of 5 volts to 12 volts at step 60 of FIG. 7B in alternative embodiments.

Figure 9A:
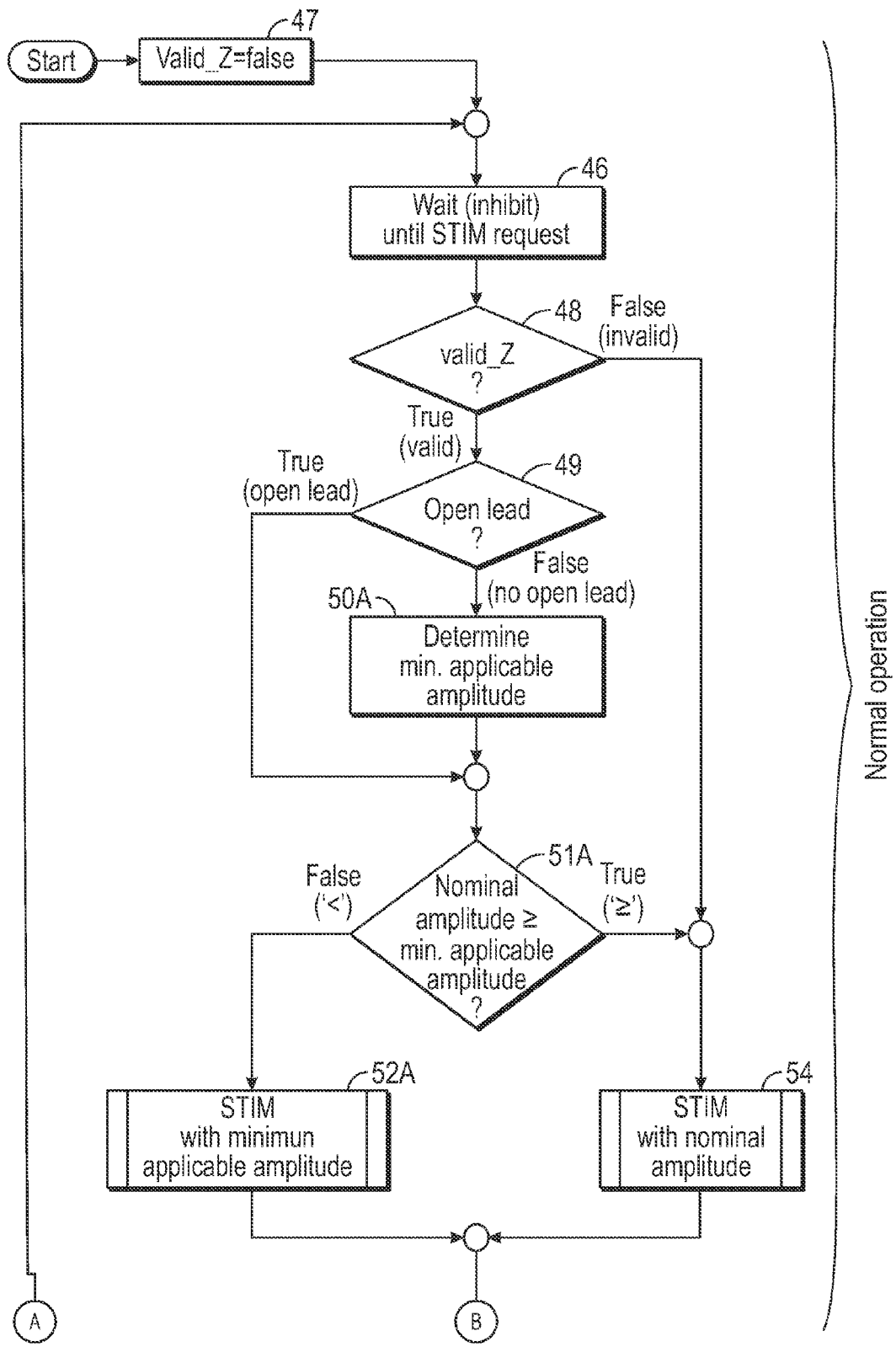
FIGS. 9A and 9B are successive parts of a flow diagram similar to that of FIGS. 7A and 7B but modified to illustrate an embodiment where current rather than voltage is the nominal amplitude set by a user.
Figure 9B:
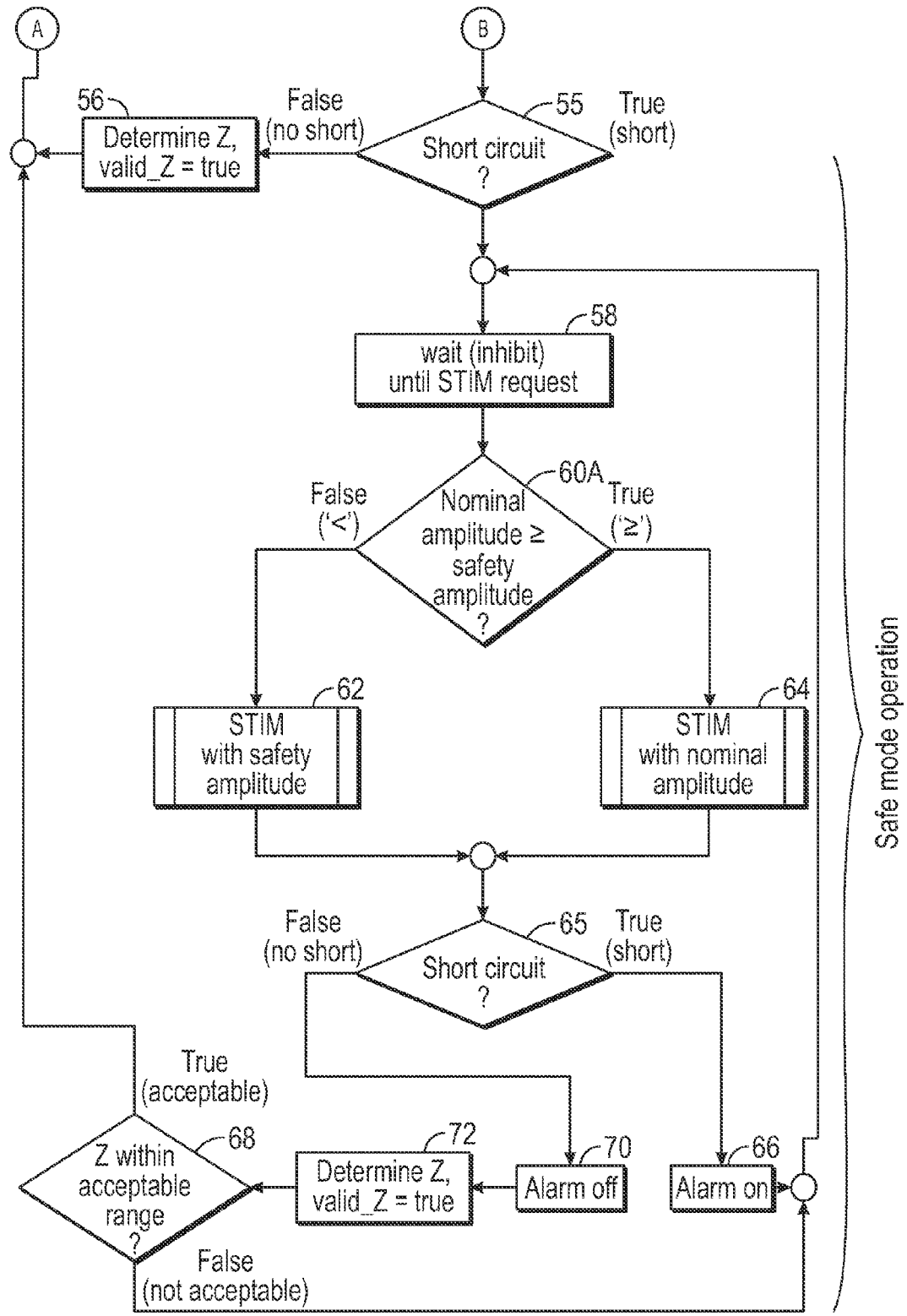
Figure 10:
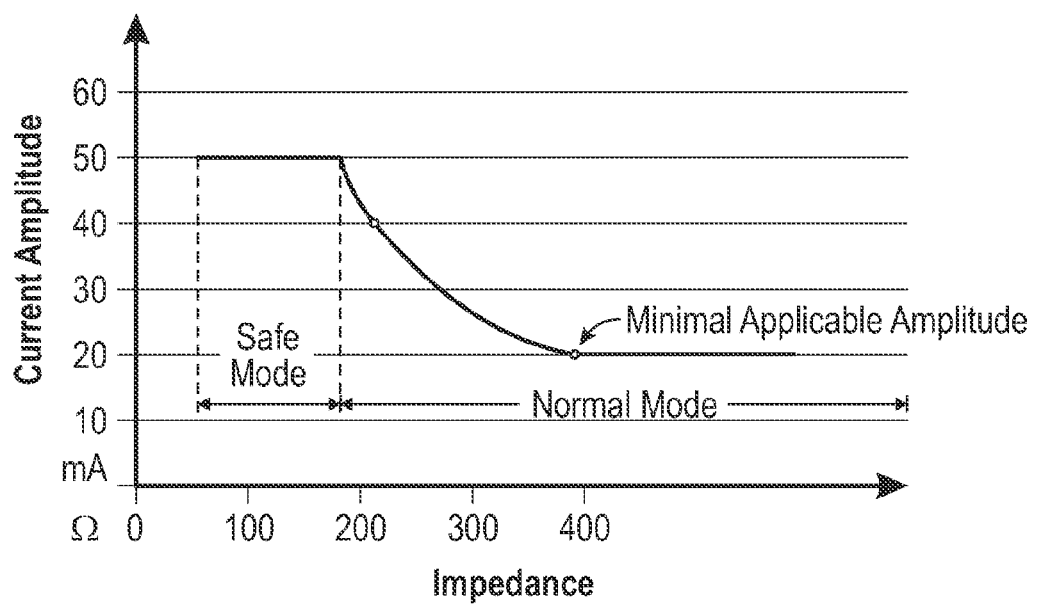
FIG. 10 is a graph illustrating variation of controllable signal amplitude with impedance in the embodiment of FIGS. 9A and 9B where the controllable signal is current, and the minimum applicable signal amplitude (e.g. current) is limited in normal and safe operation modes.

The embodiment described above in connection with FIGS. 7A to 8 is for a pulse generator in which the user controls stimulation voltage. In a pulse generator in which a user controls current amplitude, the current must be sufficient to result in a voltage amplitude sufficient for capture. FIGS. 9A and 9B illustrate a flow chart similar to FIGS. 7A and 7B but modified for an alternative embodiment where the operator controlled parameter or signal is current rather than voltage, and the minimum applicable signal amplitude (e.g. current) is limited in normal and safe modes, rather than the maximum applicable signal (voltage) as in the previous embodiment. In this embodiment, the user controls the current (measured in mA) rather than the stimulation voltage. The current may not be sufficient at excessively low impedances to generate a voltage sufficient to cause capture. FIG. 10 is a graph illustrating the current (y-axis) over impedance (x-axis) in one embodiment in which the minimum applicable current amplitude (bold black line) is limited based on the determined impedance, as in FIGS. 9A and 9B. In one embodiment, a 'Normal Mode' may be defined as the impedance range from approximately 200Ω to the upper limit of the specified range (for instance, 2,000Ω), and 'Safe Mode' is applied for impedances less than around 200Ω. However, the range may be different in alternative embodiments, depending on parameters of the pulse generator used. The current amplitude in the safe mode is set to 50 mA in this example, to increase the voltage for the most likely capture.

In this embodiment, a minimum applicable amplitude or current in the normal mode is determined or preset (step 50A of FIG. 9A). If the applied current is below this amplitude, the current needs to be increased to the minimum applicable amplitude in order to increase voltage to a sufficient level to cause capture. In the example of FIG. 10, the minimum applicable amplitude in the normal mode is 20 mA, but may different in other embodiments depending on the pulse generator. At step 51A, the system or controller determines whether the nominal amplitude or current set by the user is greater than or equal to the minimum applicable amplitude. If the detected nominal amplitude set by a user is too low at step 51A (below a minimum applicable amplitude), the system falls back to a minimum applicable amplitude (20 mA in the example of FIG. 10), and stimulates with that minimum amplitude at step 52A. If the nominal amplitude is greater than or equal to the minimum applicable amplitude, stimulation is carried out at the nominal amplitude set by the user (step 54), as illustrated for normal mode in FIG. 10.

As illustrated in FIGS. 9B and 10, the system is operated in a safety mode with a preset safety amplitude if the impedance is low. This is because the pulse generator providing a constant current set by a user may not be able to provide a stimulation voltage sufficient for capture if the impedance observed falls below the specified impedance range for the pulse generator (which may be 200 to 2000 ohms in one example). This is dependent on the particular pacemaker or pulse generator, and the safety mode current is therefore preset depending on the pacemaker parameters. In the illustrated embodiment where the lower end of the specified impedance range is 200 ohms, the safety amplitude is set at 50 mA. However, the safety amplitude may be preset at different levels from 20 to 100 mA in alternative embodiments. If it is determined that the impedance is too low at step 55 of FIG. 9B, the system switches to safe mode and determines whether the nominal amplitude is greater than the safety amplitude at the next stimulation pulse (step 60A of FIG. 9B). If the nominal amplitude is less than the safety amplitude (False), stimulation proceeds at the safety amplitude (step 62). If the nominal amplitude is equal to or greater than the safety amplitude at step 60A (True), stimulation proceeds at the nominal amplitude (step 64). The steps of FIGS. 9A and 9B are otherwise identical to those of FIGS. 7A and 7B, and like reference numbers are used for like steps as appropriate.

In each of the above embodiments, the applied stimulation voltage, current and measured impedance are provided on the output display or monitor to provide feedback to the user (doctor or other medical personnel in the case of a pacemaker).

When implementing or initially setting up a stimulation lead system connecting a patient to an external pulse generator or pacemaker, the above embodiments allow an operator to reduce the potential hazard of low impedance, by carefully choosing the arrangement of the pacing wires (e.g. removing insulation and proximity of placement) based on the output signal information in display device or window 24, providing information on the current impedance and optionally also displaying levels of applied voltage and current. Based on the impedance, a cardiac surgeon or the like can evaluate the electrical properties of the arrangement and, if needed, alter the location and/or configuration of the pacing wires in the operating room while the patient's heart is easily accessible.

Situations may arise in clinical practice where, despite all considerations, a patient requires effective stimulation therapy in the presence of a low impedance stimulation lead system. The embodiments of FIGS. 5 to 10 enable the operator to establish a better reserve in amplitude if needed for either a voltage or current controlled pulse generator, so as to overcome previous limitations of providing sufficient stimulation pulse voltage for capture in the event of a low impedance level.

Although the above embodiments describe a pulse generator for a medical application in the form of a cardiac pacemaker for cardiac rhythm management, there are other types of medical pulse generator where it may be helpful to incorporate a display device and a controller which controls the display device to display either an image showing the Ohm's law relationship between a first applied electrical signal, measured impedance, and a resulting electrical signal, or a display of current measured impedance alone. For example, the display device and display controller of the above embodiments may be incorporated in a defibrillator, or in a nerve stimulator as used in neurology. In a defibrillator application, a similar Ohm's law display of the instant current, voltage and impedance, or measured impedance alone, may be provided. In addition, the defibrillator display may also provide an image of the energy applied=voltage×current×time of application.

Those of skill will appreciate that the various illustrative logical blocks, units, modules, circuits, and algorithm steps described in connection with the embodiments disclosed herein can often be implemented as electronic hardware, computer software, or combinations of both. To clearly illustrate this interchangeability of hardware and software, various illustrative components, units, blocks, modules, circuits, and steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module, block or step is for ease of description. Specific functions or steps can be moved from one module or block without departing from the invention.

The various illustrative logical blocks, components, units, and modules described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

The steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium. An exemplary storage medium can be coupled to the processor such that the processor can read information from, and write information to, the storage medium. In the alternative, the storage medium can be integral to the processor. The processor and the storage medium can reside in an ASIC.

Various embodiments may also be implemented primarily in hardware using, for example, components such as application specific integrated circuits ("ASICs"), or field programmable gate arrays ("FPGAs"). Implementation of a hardware state machine capable of performing the functions described herein will also be apparent to those skilled in the relevant art. Various embodiments may also be implemented using a combination of both hardware and software.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly limited by nothing other than the appended claims.

We claim:

1. A monitoring and control system for a medical pulse generator, comprising:
- a control input for operator input of a selected nominal amplitude for a control parameter which varies stimulation pulse amplitude of a medical pulse generator, the control parameter comprising voltage or current;
- an impedance monitoring module configured for connection to stimulation leads of the medical pulse generator to measure impedance during a stimulation pulse;
- a short circuit detection module which is configured to detect a short circuit condition; and
- an amplitude setting control module connected to the operator control input and associated with the impedance monitoring module and short circuit detection module, the amplitude setting control module being configured to select normal mode operation or safe mode operation of the pulse generator based on input from the short circuit detection module and to set a limited nominal amplitude for normal mode operation and a predetermined safety amplitude for safe mode operation;
- wherein the system operates in normal mode when no short circuit is detected and the impedance is within predetermined minimum and maximum levels, and operates in a safe mode if a short circuit is detected;
- the nominal amplitude in the normal mode comprising the operator selected nominal amplitude up to the preset limited nominal amplitude and comprising the preset limited nominal amplitude if the operator selected nominal amplitude at the control input is greater than the preset limited nominal amplitude when the control parameter is voltage or less than the preset limited nominal amplitude when the control parameter is current;
- the amplitude in the safe mode comprising the operator selected amplitude up to the predetermined safety amplitude and comprising the predetermined safety amplitude if the operator selected amplitude is greater than the predetermined safety amplitude when the control parameter is voltage or less than the predetermined safety amplitude when the control parameter is current; and
- an alarm device, the impedance monitoring module having an output connected to the alarm device and being configured to actuate the alarm device if a short circuit is detected again during safe mode operation of the system.

2. The system of claim 1, wherein the pulse generator parameter controlled by the user comprises the stimulation pulse voltage, the preset limited nominal amplitude comprises a maximum stimulation pulse voltage for the normal mode, and the predetermined safety amplitude in the safe mode comprises a predetermined safety mode voltage less than the maximum stimulation pulse voltage, wherein the nominal amplitude in the normal mode comprises the stimulation pulse voltage set by an operator up to the maximum stimulation pulse voltage and comprises the maximum stimulation pulse voltage if the operator selected stimulation pulse voltage exceeds the maximum stimulation pulse voltage, and the stimulation pulse voltage in the safe mode comprises the operator selected voltage up to the predetermined safety mode voltage and comprises the predetermined safety mode voltage if the operator selected voltage exceeds the safety mode voltage.

3. The system of claim 2, wherein the normal mode maximum amplitude is in the range from 17 to 20 volts and the predetermined safety amplitude is in the range from 7 to 9 volts.

4. The system of claim 3, wherein the short circuit condition comprises detection of an impedance less than about 130 ohms.

5. The system of claim 4, wherein the pulse generator is a cardiac pacemaker.

6. The system of claim 1, wherein the pulse generator parameter controlled by the operator comprises a current, the preset limited nominal amplitude in the normal mode comprises a preset minimum applicable current, and the predetermined safety amplitude in the safety mode comprises a predetermined safety mode current greater than the preset minimum applicable current in the normal mode, wherein the nominal amplitude in the normal mode comprises a nominal current set by the operator if greater than or equal to the preset minimum applicable current and comprises the preset minimum applicable current if the operator selected nominal current is less than the preset minimum applicable current, and the applicable current in the safe mode comprises the operator selected nominal current if greater than or equal to the predetermined safety mode current and comprises the predetermined safety mode current if the operator selected nominal current is less than the safety mode current.

7. The system of claim 1, wherein the short circuit condition comprises at least one of a measured impedance below a predetermined level and an excess voltage or current.

8. The method of claim 7, wherein the pulse generator parameter controlled by the user comprises the stimulation pulse voltage, the preset limited nominal amplitude comprises a maximum stimulation pulse voltage for the normal mode, and the predetermined safety amplitude in the safety mode comprises a predetermined safety mode voltage less than the maximum stimulation pulse voltage, whereby, in the normal mode, a stimulation pulse is generated with an amplitude comprising the nominal voltage amplitude set by an operator up to the maximum stimulation pulse voltage and a stimulation pulse is generated at the maximum stimulation pulse voltage if the operator selected nominal voltage amplitude exceeds the maximum stimulation pulse voltage, and in the safe mode, a stimulation pulse is generated at the operator selected nominal amplitude up to the predetermined safety mode voltage and at the predetermined safety mode voltage if the operator selected nominal amplitude exceeds the safety mode voltage.

9. The method of claim 7, wherein the pulse generator parameter controlled by the operator comprises a current, the stimulation pulse voltage amplitude varying dependent on the operator controlled current, the preset limited nominal amplitude in the normal mode comprises a preset minimum applicable current, and the predetermined safety amplitude in the safety mode comprises a predetermined safety mode current greater than the minimum applicable current in the normal mode, whereby, in the normal mode, a stimulation pulse is generated using the nominal current set by an operator up to the preset minimum applicable current and a stimulation pulse is generated using the preset minimum applicable current if the operator selected nominal current is less than the preset minimum applicable current, and in the safety mode, a stimulation pulse is generated using the operator selected nominal current up to the predetermined safety mode current and using the predetermined safety mode current if the operator selected nominal current is less than the safety mode current.

10. A method of controlling operation of a medical pulse generator, comprising:

monitoring a nominal amplitude of a pulse generator parameter set by an operator of a medical pulse generator, the parameter comprising a stimulation voltage or a current;

measuring impedance across pacing wires of the medical pulse generator at each stimulation pulse;

monitoring one or more pulse generator parameters to detect a short circuit condition;

selecting a normal mode operation of the pulse generator when no short circuit condition is detected and the measured impedance following a stimulation pulse is within predetermined minimum and maximum levels, and selecting safe mode operation when a short circuit condition is detected, setting a limited nominal amplitude for normal mode operation and a predetermined safety amplitude for safe mode operation;

in the normal mode, generating a stimulation pulse of amplitude depending on a nominal amplitude set by an operator up to the preset limited nominal amplitude and generating a stimulation pulse using the preset limited nominal amplitude if the operator selected nominal amplitude is greater than the preset limited nominal amplitude when the pulse generator parameter is voltage and less than the preset limited nominal amplitude when the pulse generator parameter is current;

in the safe mode, generating a stimulation pulse using the operator selected nominal amplitude up to the predetermined safety amplitude and generating a stimulation pulse using the predetermined safety amplitude if the operator selected nominal amplitude is greater than the predetermined safety amplitude when the pulse generator parameter is voltage and less than the predetermined safety amplitude when the pulse generator parameter is current; and actuating an alarm device if a short circuit is detected again during safe mode operation of the system.

11. The system of claim 10, wherein the pulse generator is a temporary external cardiac pacemaker.

12. A medical pulse generator system, comprising:

a pulse generator configured to generate stimulation pulses;

a stimulation pulse controller configured to control the pulse generator to generate a stimulation pulse;

the stimulation pulse controller having a control input for operator selection of a nominal amplitude for a control parameter which varies the stimulation pulse, the control parameter comprising voltage or current;

a lead system configured to connect a stimulation pulse output of the pulse generator to a patient at a tissue interface;

an impedance measurement module connected to the lead system and configured to measure impedance following a stimulation pulse;

a short circuit detection module configured to detect a short circuit condition;

an amplitude setting module connected to the user control input and associated with the impedance monitoring module and short circuit detection module, the amplitude setting control module being configured to select normal mode operation or safe mode operation of the pulse generator based on input from the short circuit detection module and to set a limited nominal amplitude for normal mode operation based on the detected impedance following a previous stimulation pulse and to set a predetermined safety amplitude for safe mode operation;

wherein the system operates in normal mode when no short circuit is detected and the impedance is within predetermined minimum and maximum levels, and operates in a safe mode if a short circuit is detected;

the nominal amplitude in the normal mode comprising the operator selected nominal amplitude up to the preset limited nominal amplitude and comprising the preset limited nominal amplitude if the operator selected nominal amplitude at the control input exceeds the preset limited nominal amplitude when the control parameter is voltage and is less than the preset limited nominal amplitude when the control parameter is current;

the stimulation pulse amplitude in the safe mode comprising the operator selected amplitude up to the predetermined safety amplitude and comprising the predetermined safety amplitude if the operator selected amplitude exceeds the predetermined safety amplitude when the control parameter is voltage and is less than the predetermined safety amplitude when the control parameter is current; and an alarm device, the impedance measurement module having an output connected to the alarm device and being configured to actuate the alarm device if a short circuit is detected again during safe mode operation of the system.

13. A monitoring and control system for a medical pulse generator, comprising:

a control input for operator input of a selected nominal amplitude for a control parameter which varies stimulation pulse amplitude of a medical pulse generator, the control parameter comprising voltage or current;

an impedance monitoring module configured for connection to stimulation leads of the medical pulse generator to measure impedance during a stimulation pulse;

a short circuit detection module which is configured to detect a short circuit condition; and an amplitude setting control module connected to the operator control input and associated with the impedance monitoring module and short circuit detection module, the amplitude setting control module being configured to select normal mode operation or safe mode operation of the pulse generator based on input from the short circuit detection module and to set a limited nominal amplitude for normal mode operation and a predetermined safety amplitude for safe mode operation;

wherein the system operates in normal mode when no short circuit is detected and the impedance is within predetermined minimum and maximum levels, and operates in a safe mode if a short circuit is detected;

the nominal amplitude in the normal mode comprising the operator selected nominal amplitude up to the preset limited nominal amplitude and comprising the preset limited nominal amplitude if the operator selected nominal amplitude at the control input is greater than the preset limited nominal amplitude when the control parameter is voltage or less than the preset limited nominal amplitude when the control parameter is current; and the amplitude in the safe mode comprising the operator selected amplitude up to the predetermined safety amplitude and comprising the predetermined safety amplitude if the operator selected amplitude is greater than the predetermined safety amplitude when the control parameter is voltage or less than the predetermined safety amplitude when the control parameter is current;

wherein the pulse generator parameter controlled by the operator comprises a current, the preset limited nominal amplitude in the normal mode comprises a preset minimum applicable current, and the predetermined safety amplitude in the safety mode comprises a predetermined safety mode current greater than the preset minimum applicable current in the normal mode, wherein the nominal amplitude in the normal mode comprises a nominal current set by the operator if greater than or equal to the preset minimum applicable current and comprises the preset minimum applicable current if the operator selected nominal current is less than the preset minimum applicable current, and the applicable current in the safe mode comprises the operator selected nominal current if greater than or equal to the predetermined safety mode current and comprises the predetermined safety mode current if the operator selected nominal current is less than the safety mode current.

14. A monitoring and control system for a medical pulse generator, comprising:

a control input for operator input of a selected nominal amplitude for a control parameter which varies stimulation pulse amplitude of a medical pulse generator, the control parameter comprising voltage or current;

an impedance monitoring module configured for connection to stimulation leads of the medical pulse generator to measure impedance during a stimulation pulse;

a short circuit detection module which is configured to detect a short circuit condition; and an amplitude setting control module connected to the operator control input and associated with the impedance monitoring module and short circuit detection module, the amplitude setting control module being configured to select normal mode operation or safe mode operation of the pulse generator based on input from the short circuit detection module and to set a limited nominal amplitude for normal mode operation and a predetermined safety amplitude for safe mode operation;

wherein the system operates in normal mode when no short circuit is detected and the impedance is within predetermined minimum and maximum levels, and operates in a safe mode if a short circuit is detected;

the nominal amplitude in the normal mode comprising the operator selected nominal amplitude up to the preset limited nominal amplitude and comprising the preset limited nominal amplitude if the operator selected nominal amplitude at the control input is greater than the preset limited nominal amplitude when the control parameter is voltage or less than the preset limited nominal amplitude when the control parameter is current; and the amplitude in the safe mode comprising the operator selected amplitude up to the predetermined safety amplitude and comprising the predetermined safety amplitude if the operator selected amplitude is greater than the predetermined safety amplitude when the control parameter is voltage or less than the predetermined safety amplitude when the control parameter is current;

wherein the pulse generator parameter controlled by the user comprises the stimulation pulse voltage, the preset limited nominal amplitude comprises a maximum stimulation pulse voltage for the normal mode, and the predetermined safety amplitude in the safe mode comprises a predetermined safety mode voltage less than the maximum stimulation pulse voltage, wherein the nominal amplitude in the normal mode comprises the stimulation pulse voltage set by an operator up to the maximum stimulation pulse voltage and comprises the maximum stimulation pulse voltage if the operator selected stimulation pulse voltage exceeds the maximum stimulation pulse voltage, and the stimulation pulse voltage in the safe mode comprises the operator selected voltage up to the predetermined safety mode voltage and comprises the predetermined safety mode voltage if the operator selected voltage exceeds the safety mode voltage; and wherein the normal mode maximum amplitude is in the range from 17 to 20 volts and the predetermined safety amplitude is in the range from 7 to 9 volts.

* * * * *